United States Patent [19]

Marten et al.

[11] 4,358,854
[45] Nov. 9, 1982

[54] MEASURING DEVICES FOR X-RAY FLUORESCENCE ANALYSIS

[75] Inventors: Rainer Marten; Herbert Rosomm, both of Geesthacht; Heinrich Schwenke, Escheburg, all of Fed. Rep. of Germany

[73] Assignee: Gesellschaft für Kernenergieverwertung in Schiffbau und Schiffahrt mbH, Geesthact-Tesperhude, Fed. Rep. of Germany

[21] Appl. No.: 214,636

[22] Filed: Dec. 10, 1980

Related U.S. Application Data

[63] Continuation-in-part of Ser. No. 974,551, Dec. 29, 1978, abandoned, which is a continuation of Ser. No. 816,862, Jul. 18, 1977, abandoned.

[30] Foreign Application Priority Data

Jul. 16, 1976 [DE] Fed. Rep. of Germany ....... 2632001

[51] Int. Cl.³ .......................................... G01M 23/22
[52] U.S. Cl. ......................................... 378/45; 378/79
[58] Field of Search ......... 250/272, 273, 274, 277 CH

[56] References Cited

U.S. PATENT DOCUMENTS 3,391,276 7/1968 Delarue ...................... 250/277 CH
3,649,831 3/1972 Eckerlin ...................... 250/277 CH
4,169,228 9/1979 Briska ................................. 250/272

*Primary Examiner*—Craig E. Church
*Attorney, Agent, or Firm*—Becker & Becker, Inc.

[57] ABSTRACT

A measuring device for X-ray fluorescence analysis, in which a specimen disposed on a carrier is stimulated by glancing incident radiation and examined spectrometrically by a detector which may be arranged above the specimen. On the upper side of an e.g., box-shaped housing in which a vacuum can be created, there is provided a detector extending into the interior of the housing. This detector is connected to the housing by means of a pivotable frame within the housing. The pivot axis of the frame is located in the measuring plane of the detector. Provided on the pivotable frame is a remote controllable specimen exchanger and a remote controllable disengaging device for shifting the specimen carrier out of its operative position, the disengaging device being substantially aligned with the detector axis. The pivotable frame has furthermore provided thereon counter bearings for the specimen carriers; these counter bearings surround the measuring region. In one side wall of the housing there is provided a ray inlet window which is aligned with the measuring plane. This window is for a radiation source which can be placed externally in front of the housing.

9 Claims, 1 Drawing Figure

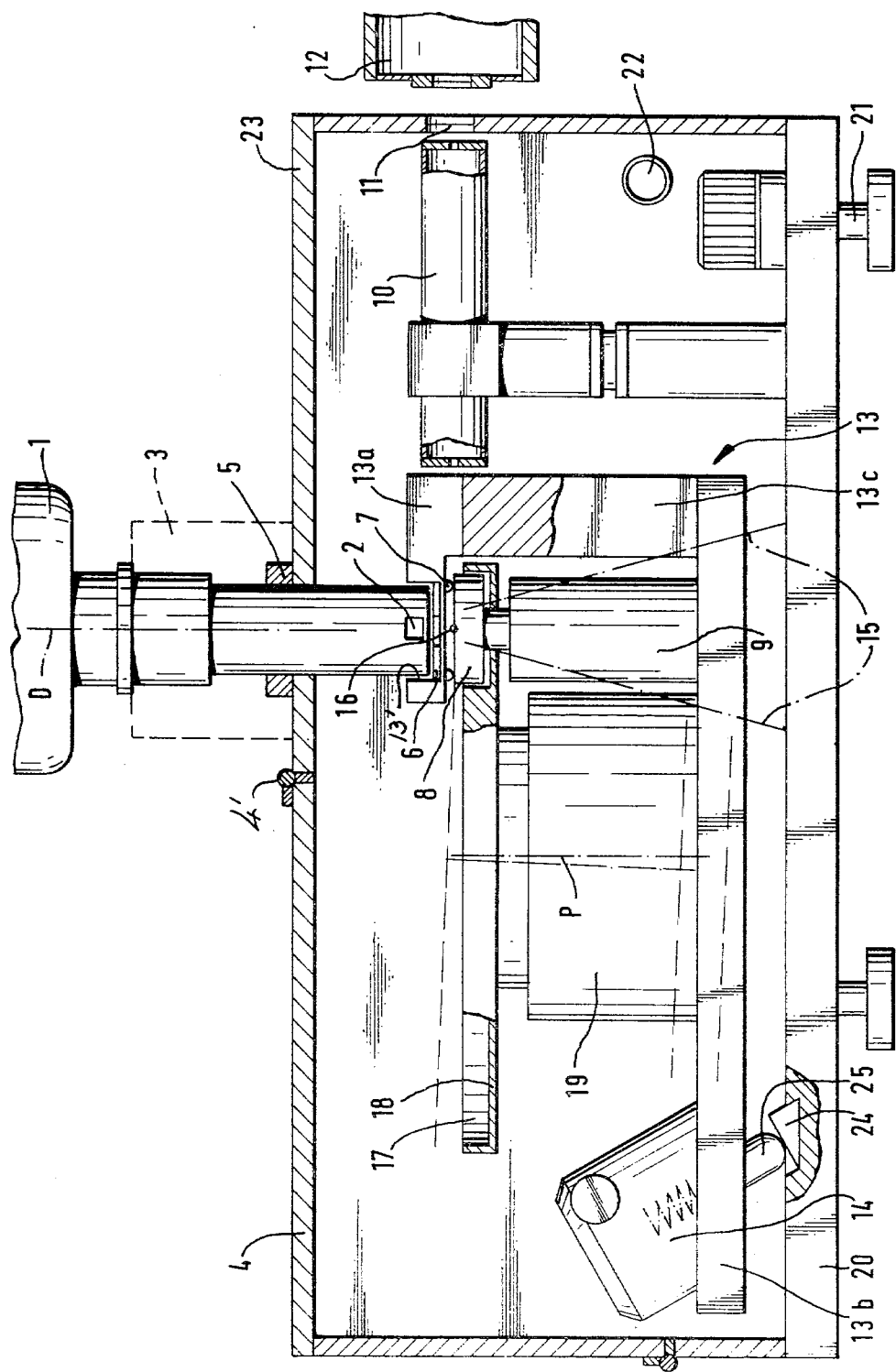

MEASURING DEVICES FOR X-RAY FLUORESCENCE ANALYSIS

This is a continuation-in-part application based upon co-pending application Ser. No. 974,551-Marten et al. filed Dec. 29, 1978 now abandoned as a straight continuation of then co-pending application Ser. No. 816,862-Marten et al. filed July 18, 1977 now abandoned.

The present invention relates to a measuring device for X-ray fluorescence analysis, wherein the specimen disposed on a support is stimulated by glancing or touching incident radiation and is examined spectrometrically by a detector.

The measuring devices heretofore known for X-ray fluorescence analysis with totally reflecting specimen supports were very complex in construction; they were assembled on an optical bench in each case and therefore required a very large space for installation and frequently tended to get out of adjustment. Such lack of adjustment related above all to the angle which the incident radiation formed with the surface of the specimen.

It is, therefore, an object of the present invention to so develop a measuring device of the kind referred to above that it can be used with high operating confort, in a particularly simple manner, for series examinations, can be stored in a minimum of space and is available for use at any time without a tedious assembly being necessary.

These and other objects and advantages of the invention will appear more clearly from the following specification in connection with the accompanying drawing diagrammatically illustrating a longitudinal section through a measuring device according to the present invention.

With the measuring device for X-ray fluorescence analysis according to the present invention, a specimen is disposed on a carrier and is stimulated by glancing incident radiation and examined spectrometrically by a detector. The device according to the invention is characterized primarily in that it comprises an evacuatable housing; a detector having a detector axis with a measuring region in the interior of the housing; a window in the housing aligned with the measuring region for cooperation with an external X-ray source; a frame pivotally mounted in the housing about an axis lying in the measuring region normal to the detector axis; abutment means provided on the frame for locating a specimen carrier in the measuring region, and means provided on the frame for supporting a plurality of specimen carriers and for directing a selected one of the specimen carriers into engagement with the abutments.

Referring now to the drawing in detail, the detector system of the measuring device consists in a manner known per se of a Dewar vessel 1 with a SiLi detector in a holder 3 which latter is inserted with a seal 5, in the hood 23 of a housing. The hood 23 rests at its lower edge, with a sealing action on a base plate 20. In the hood 23 there is a loading flap 4 which is hinged at 4' to hood 23, and which can likewise be closed in a substantially gas-tight manner. The detector is held inside the seal 5 for adjustment with respect to its detector axis D.

The gas-tight closure of the housing consisting of hood 23, cover 4 and base plate 20 affords the possibility of evacuating the housing or filling it or scavenging it with gases, for example with helium.

At the side in the hood there is an entry window 11 of beryllium. An external radiation source 12 can be placed in front of this window and may be an X-ray tube or a secondary target for example. The beryllium window 11 insures that the stimulating X-radiation is weakened as little as possible. The SiLi diode illustrated in the drawing may also be replaced by another detector for the analysis of X-radiation, for example a counter tube or an NaJ crystal. As a result of the fact that the radiation source 12 is provided outside the housing 23, there exists the possibility of setting up the measuring device according to the invention to replace another measuring device at a suitable existing radiation source and of removing it when required. Behind the entry window 11 there are anti-diffusing screens 10 which are supported by a pedestal on the base plate 20.

An essential part of the present invention is the pivotable frame 13 mounted on the base plate 20. This pivoted frame consists of a short upper arm 13a, a longer lower arm 13b and yoke member 13c connecting the two arms 13a, 13b. The two arms 13a and 13b extend substantially parallel to one another, more or less parallel to the base plate 20. The pivotable frame 13 is mounted on the base plate 20 with a two-part bearing block 15, the pivotable axis 16 of which extends through the measuring region perpendicular to the plane of the paper in the accompanying drawing. The region where the radiation coming from the radiation source 12 intersects the detector axis D is here designated as the measuring region. The two halves of the bearing block 15 are disposed on the base plate 20 so that they do not hamper the pivotable frame 13, the parts carried by this frame and to be described later, and the detector system.

The upper arm 13a of the frame 13 comprises an aperture 13' which surrounds the front end of the detector 2 with slight clearance. At the inside of the arm 13a, at the edge of said aperture 13', there are ball-shaped abutments 7 which define the measuring plane and against which the specimen-carrier plates 8 come to bear in a manner which will be described below. In this manner, the entry window of the detector system 1, 2 can be disposed immediately above the specimen carrier plate 8. A separate diaphram 6 of the detector system defines the aperture of the detector. The adaptation and adjustment of the detector system is effected by means of the adjustable holder 3, as already mentioned above.

In its upper region, that is to say in the region of the upper arm 13a, the pivoted frame 13 is provided with a recess through which the radiation from the radiation source 12 can reach the measuring plane. The outer region of the radiation field is masked with diaphrams 10 so as to keep scattered radiation away from the specimen site.

The lower arm 13b of the pivoted frame 13 carries a specimen changer which consists of a positioning device 19 and a rotary plate 18 which is rotatable like a turn-table about the axis P and which can receive a specimen magazine 17. The positioning device can be turned by means of a drive which can be operated from the outside so that the specimen carrier plates contained in the specimen magazine 17 in succession can be aligned with the detector axis D. As the drawing shows, the individual specimen carrier plates 8 lie with slight clearance in recesses in the specimen magazine 17. Beside the positioning device 19, there is a pressure device 9 which can likewise be moved by a drive which can be operated from the outside, just like the positioning device 19. On activation of the pressure device 9, a ram presses from below through the rotary plate 18 and then displaces the specimen carrier plate 8 towards the point abutments 7 into a position precisely defined by the upper arm 13a, in front of the detector axis D. With regard to its lifting movements, the pressure device is substantially aligned with the detector axis D.

The end of the lower arm 13b situated at the left in the drawing is supported by a micrometer screw 14 on an abutment 24 of the base plate. The micrometer screw 14 is set tangentially with respect to the pivotal axis 16 and bears against an abutment 24 of the base plate, the supporting surface of which is aligned substantially radially with respect to the pivotal axis 16. The micrometer screw 14 can be adjusted by a spindle 25 which can be operated manually or by remote control. In this manner, the angle between the radiation axis and the specimen carrier plate 8 can be adjusted within a range of a few angle minutes. The firm bearing of the micrometer screw 14 against the abutment 24 is assured as a result of the fact that the weight of the specimen changing system exerts a moment with respect to the pivotal axis 16, which is effective in counterclockwise direction with respect to the drawing. As a result of the selected position of the pivotal axis 16, the specimen remains at the same place in the radiation field even on rotation of the pivoted frame and hence of the specimen carrier plate. These specimen carrier plates 8 are precision machined at their surface and consist of very pure quartz glass for example.

One or more adjustable legs 21 serve to adjust the base plate 20 in relation to a mounting or table plate. A vacuum connection 22, which may be of conventional construction and which renders possible a connection to a vacuum or gas source, serves to evacuate the housing 23 or to scavenge it with gas.

A measuring series with a relatively large number of specimens can be examined automatically with the measuring device according to the invention. For this purpose, a specimen magazine with a plurality of specimen carrier plates is placed on the rotary plate 18. After the housing 23 has been closed and a radiation source 12 has been placed in front and after a vacuum or a filling of gas has been produced, the series measurement can be carried out. The individual specimen carrier plates are brought into the measuring position, either controlled by a program or manually, by means of the positioning device 19. Since the specimen carrier plates lie in a replaceable magazine, further measuring series can be prepared while the measurements are in progress. This includes cleaning operations (for example in various ultrasonic baths) and the loading of the carrier plates with specimen material (measuring out with microliter pipettes, production of thin layers). The hood 23 of the device preferably consists of transparent material so that the measuring process can be observed visually.

Commercial electronics are used for the control of the positioning system and for the signal preparation of the detector system. According to the problem posed, the spectrum of apparatus ranges from economical individual components to computer-controlled and checked analysis systems.

Thus, for the first time, the present invention provides a technical solution which enables the effect of total reflection of the X-radiation to be used with the ease of operation necessary for routine examinations. The effect of background reduction by total reflection of the incident X-radiation has long since been proved but the measuring devices hitherto used to utilize the above-mentioned effect were exclusively laboratory installations which were unsuitable for routine use because they can only be adjusted with difficulty and they do not permit any automatic changing of the specimens.

The present invention comprises a very precise angle setting of a quartz-glass surface which is imperative to fullfill the total reflection of the incident X-ray beam in connection with a device to transport a plurality of quartz blocks into the exactly defined position.

It is, of course, to be understood that the present invention is, by no means, limited to the specific showing in the drawing but also comprises any modifications within the scope of the appended claims.

What we claim is:

1. An apparatus including carrier plates for fluorescence analysis of specimens comprising in combination: U-formed supporting and positioning means for a specimen carrier plate having a plane surface, including abutment means defining a plane for engaging the plane surface of the specimen carrier plate with the plane surface of said plate coincident with the plane defined by said abutment means, said abutment means being mounted for pivotal movement about a pivotal axis lying in said plane defined by said abutment means, a detector for detection of radiation having a detector axis perpendicular to said pivotal axis of said abutment means and passing through said plane defined by said abutment means, means for directing X-ray radiation along a radiation axis substantially perpendicular to said pivotal axis and to said detector axis to form a measuring region in which radiation is directed to said plane defined by said abutment means, pressure means to position said specimen carrier plate with its plane surface in engagement with said abutment means so that said plane surface and the plane defined by said abutment means coincide, and means to adjust said abutment means about said pivotal axis to vary the angle of said plane defined by said abutment means and the plane surface on said specimen carrier plate, so that said plane surface on said specimen carrier plate may be angularly adjusted precisely relative to said radiation axis.

2. An apparatus including carrier plates for fluorescence analysis of specimens comprising in combination: a substantially gas-tight housing, supporting and positioning means in said housing for specimen carrier plates having plane surfaces, including abutment means defining a plane for engaging the plane surface of a specimen carrier plate with the plane surface of said plate coincident with the plane defined by said abutment means, said abutment means being mounted for pivotal movement about a pivotal axis lying in said plane defined by said abutment means, a detector for detection of radiation mounted on and projecting through a wall of said housing and having a detector axis perpendicular to said pivotal axis of said abutment means and passing through said plane defined by said abutment means, means for directing X-ray radiation along a radiation axis perpendicular to said pivotal axis and said detector axis to form a measuring region in which radiation is directed to said plane defined by said abutment means and including a radiation entry window in a wall of said housing for passage of said radiation from outside of said housing, said supporting and positioning means including a movable holder for a plurality of specimen carrier plates, said holder being movable to move each specimen carrier plate to said measuring region, pressure means to move said specimen carrier plate to engage its plane surface with said abutment means so that said plane surface and plane defined by said abutment means coincide and means to adjust said abutment means about said pivotal axis to vary the angle of said plane defined by said abutment means and the plane surface of said specimen carrier plate, so that said plane surface on each specimen carrier plate may be angularly adjusted precisely relative to said radiation axis.

3. An apparatus including carrier plates for fluorescence analysis of specimens comprising in combination: a substantially gas-tight evacuatable housing, U-formed supporting and positioning means in said housing as a pivot frame including an upper short arm with an underside connected by way of a vertical yoke member to a lower longer arm for specimen carrier plates having plane surfaces, including abutment means defining a measuring plane and located at the underside of said upper arm for engaging the plane surface of a specimen carrier plate with the plane surface of said plate coincident with the plane defined by said abutment means, said U-formed supporting and positioning means as the pivot frame including said abutment means being mounted for pivotal movement about a pivotal axis thereof lying in said plane defined by said abutment means, a detector for detection of radiation mounted on and projecting through a wall of said housing and having a detector axis perpendicular to said pivotal axis of said supporting and positioning means and passing through said plane defined by said abutment means, means for directing X-ray radiation along a radiation axis perpendicular to said pivotal axis and said detector axis to form a measuring region in which radiation is directed to said plane defined by said abutment means and including a radiation entry window in a wall of said housing for passage of said radiation from outside of said housing, said supporting and positioning means including a movable holder for a plurality of specimen carrier plates to said measuring region, pressure means carried by said lower longer arm of the pivot frame to move said specimen carrier plate to engage its plane surface with said abutment means to that said plane surface and plane defined by said abutment means coincide, and adjustment screw means operable from outside said housing to adjust said supporting and positioning means with said abutment means about said pivotal axis to vary the angle of said plane defined by said abutment means and the plane surface of said carrier plate relative to said radiation axis, so that said plane surface on each specimen carrier plate may be angularly adjusted precisely relative to said radiation axis, and means operable from outside said housing to move said holder to position each plate in said measuring region, and means to actuate said means to engage each specimen carrier plate with said abutment means.

4. An apparatus in combination as claimed in claim 2, in which said holder is movable in a plane perpendicular to said detector axis to place each specimen carrier plate in said measuring region and said means to move said specimen carrier plate to engage its plane surface with said abutment means is movable parallel to said detector axis.

5. An apparatus in combination as claimed in claim 4, in which said plane surface of said specimen carrier plate is a totally reflecting specimen support surface when positioned at a slight angle to said radiation axis by adjustment of said abutment means, so that radiation along said radiation axis may be totally reflected by said surface, and the specimen on said surface receives said radiation directly and by reflection from said plane surface.

6. An apparatus in combination as claimed in claim 4, in which means is provided for moving said holder from outside of said housing and the means for moving said specimen carrier plate into engagement with said abutment means is operable from outside of said housing.

7. The method of fluorescence analysis of a specimen on a totally reflecting plane surface using X-ray radiation striking said specimen at a glancing angle to said plane surface to cause total reflection, and detecting radiation from the specimen on said totally reflecting surface by a detector having a detector axis passing through said specimen, said method in combination comprising: directing X-ray radiation on an axis intersecting the axis of said detector to form a measuring region at said intersection, moving a specimen carrier plate having a totally reflecting plane surface into a position traversed by said detector axis, moving said carrier plate in said position traversed by said detector axis into contact with abutment means which define a plane traversed by said axis of said detector so that said X-ray radiation irradiating a specimen strikes said plane surface of said specimen carrier plate, and adjusting said abutment means about an axis in the plane of said abutment means in said measuring region to vary the angle of the plane surface of said carrier plate to the axis of said X-ray radiation.

8. The method of fluorescence analysis of a plurality of specimens on totally reflecting plane surfaces of specimen carrier plates with X-ray radiation irradiating and striking each specimen at a glancing angle to said plane surface to produce total reflection from the surface, and detecting radiation from the specimen by a detector having a detector axis passing through the specimen, said method in combination comprising directing X-ray radiation on a radiation axis intersecting the axis of said detector to form a measuring region at said intersection, moving said specimen carrier plates having totally reflecting plane surfaces in a plane perpendicular to said detector axis successively into a position traversed by said detector axis, adjusting abutment means defining a plane in said measuring region and pivotal about an axis in said plane and perpendicular to said detector axis and said radiation axis, said abutment means being angularly adjustable relative to said radiation axis, moving each carrier plate traversed by said detector axis into contact with said abutment means with its plane surface coincident with the plane defined by said abutment means, so that each specimen carrier plate may be positioned with its totally reflecting plane surface in the plane defined by said abutment means at a small angle to said radiation axis with the specimen irradiated on said plane surface under direct X-ray radiation and radiation reflected by said totally reflecting surface.

9. An apparatus according to claim 1 further comprising a magazine having a plurality of specimen carrier plates seated thereon, means to move said magazine to present said specimen carrier plates with specimens thereon successively to said measuring region and below and opposite said abutment means, pressure means actuatable to move each specimen carrier plate transversely to the movement of said magazine and upwardly into engagement with said abutment means with the surface of said plate and specimen thereon in the plane defined by said abutment means, so that said detector may receive radiation from a specimen on said plate.

* * * * *